United States Patent [19]
Landegren et al.

[11] Patent Number: 5,871,921
[45] Date of Patent: Feb. 16, 1999

[54] CIRCULARIZING NUCLEIC ACID PROBE ABLE TO INTERLOCK WITH A TARGET SEQUENCE THROUGH CATENATION

[76] Inventors: Ulf Landegren, Eksoppsvägen 16, S-756 46 Uppsala; Marek Kwiatkowski, Lövsångarvägen 17, S-756 52 Uppsala, both of Sweden

[21] Appl. No.: 693,302
[22] PCT Filed: Feb. 16, 1995
[86] PCT No.: PCT/SE95/00163
  § 371 Date: Aug. 23, 1996
  § 102(e) Date: Aug. 23, 1996
[87] PCT Pub. No.: WO95/22623
  PCT Pub. Date: Aug. 24, 1995

[30] Foreign Application Priority Data

Feb. 16, 1994 [SE] Sweden .................................. 9400522

[51] Int. Cl.⁶ ...................................................... C12Q 1/68
[52] U.S. Cl. .................................. 435/6; 935/77; 935/78
[58] Field of Search .................................. 435/6, 15, 29, 435/91.52, 18, 77, 78; 536/24.3, 25.32

[56] References Cited

U.S. PATENT DOCUMENTS

| | | | |
|---|---|---|---|
| 4,808,519 | 2/1989 | Hartley et al. ................................ | 435/6 |
| 4,883,750 | 11/1989 | Whiteley et al. ............................ | 435/6 |
| 4,988,617 | 1/1991 | Landegren et al. .......................... | 435/6 |
| 5,242,794 | 9/1993 | Whiteley et al. ............................ | 435/6 |
| 5,426,180 | 6/1995 | Kool ....................................... | 536/25.3 |
| 5,516,663 | 5/1996 | Backman et al. ....................... | 435/91.2 |

FOREIGN PATENT DOCUMENTS

| | | |
|---|---|---|
| 0 185 494 A2 | 6/1986 | European Pat. Off. . |
| 0 320 308 A2 | 6/1989 | European Pat. Off. . |
| 0 324 616 A2 | 7/1989 | European Pat. Off. . |
| 0 336 731 A2 | 10/1989 | European Pat. Off. . |
| 0 473 155 A2 | 3/1992 | European Pat. Off. . |
| 4-262799 | 9/1992 | Japan . |
| 4-304900 | 10/1992 | Japan . |
| WO 90/01548 | 2/1990 | WIPO . |
| WO 96/14406 | 5/1996 | WIPO . |

OTHER PUBLICATIONS

Fischer, S. et al., "Integrated Mapping of YAC and Cosmid Contigs of Human Chromosome 13," in: Abstracts of papers presented at the 1994 meeting on Genome Mapping and Sequencing, Cold Spring Harbor Laboratory, Cold Spring Harbor, NY, May 11–15, 1994, Cold Spring Harbor Laboratory Meetings Dept., Pub., p. 67 (May 1994).

Nilsson, M. et al., "Padlock Probes: Circularizing Oligonucleotides for Localized DNA Detection," *Science* 265:2085–2088 (Sep. 1994).

Nilsson, M. et al., "Padlock–Probes for in stitu Detection of Gene Sequences," in: Abstracts of papers presented at the 1994 meeting on Genome Mapping and Sequencing, Cold Spring Harbor Laboratory, Cold Spring Harbor, NY, May 11–15, 1994, Cold Spring Harbor Laboratory Meetings Dept., p. 190 (May 1994).

Nilsson, M. et al., "Padlock–Probes for in stitu Detection of Gene Sequences," Summary of poster presented at the 1994 Meeting on Genome Sequencing and Mapping, Cold Spring Harbor Laboratory, Cold Spring Harbor, New York, p. 1–3 (May 1994).

(List continued on next page.)

Primary Examiner—Lisa B. Arthur
Attorney, Agent, or Firm—Sterne, Kessler, Goldstein & Fox P.L.L.C.

[57] ABSTRACT

The invention relates to a method of detecting a target nucleic acid sequence in a sample by contacting the sample with a detectable probe having ends which hybridize to two adjacent regions of the target sequence. The hybridized probe ends are then covalently connected to form a cyclized structure interlocking with the target molecule. This structure is then subjected either to non-hybridizing conditions and/or to exonuclease activity to remove any non-cyclized probes from the target sequence. The target molecule is then detected by detecting the presence of the interlocking, cantenated probe.

46 Claims, 4 Drawing Sheets

OTHER PUBLICATIONS

Zhang, P. et al., "Statistical Distance Approach for the Orientation and Ordering of Multiple Non–overlapping Contigs," in: Abstracts of papers presented at the 1994 meeting on Genome Mapping and Sequencing, Cold Spring Harbor Laboratory, Cold Spring Harbor, NY, May 11–15, 1994, Cold Spring Harbor Laboratory Meetings Dept. Pub., p. 290 (May 1994).

Jäschke, A. et al., "Automated Incorporation of Polyethylene Glycol into Synthetic Oligonucleotides," *Tetra. Lett.* 34(2):301–304 (Jan. 1993).

Sund, C. et al., "Construction of Europium (Eu3+)—Labelled Oligo DNA Hybridization Probes," *Nucleosid. & Nucleotid.* 7(5 and 6):655–659 (1988).

International Search Report for PCT/SE95/00163.

Dialog World Patent Index 351 English Language Abstract JP 4–262799, Dialog accession No. 009233973.

Dialog World Patent Index 351 English Language Abstract for JP 4–304900, Dialog accession No. 009282380.

```
         CCCGG CCTAG CTCTA GACTC CAGGC CATGC AAGCT TGCCA CGGCC
         GCCAG TGCCA AGCTT GCATG CCTGC AGGTC GACTC TAGAG GATCC CCGGG
AAAAA                                                              AAAAA
  5                          50                                5
     TATAAGTAGTATCCTT-P   TGTCGTTTCTATCTATAA-P   ACAAATTACCACGGGTC
         16                     17                     16
```

FIG.3

```
                              M13
                    CCCGGGATCCTCTAGAGTCGACCTGCAGG
AAAAA            CCTGCAGGTCGACTCTAGAGGATCCCCGGG            AAAAA   70-mer
                              CF Δ508
                    AGAAAATATCATCTT P-TGGTG TTTCC TATGA
```

CIRCULARIZING NUCLEIC ACID PROBE ABLE TO INTERLOCK WITH A TARGET SEQUENCE THROUGH CATENATION

This application was filed under 35 U.S.C. 371 from PCT/SE95/00163 on Feb. 16, 1995.

BACKGROUND OF THE INVENTION

1. Field of the Invention

The present invention relates to a novel method of detecting specific nucleic acid sequences as well as a detecting reagent and kit therefor.

2. Related Art

The isolation of enzymes that can join separate DNA molecules was fundamental to the development of recombinant DNA technology. Using these enzymes, called ligases, genetic elements derived from different genomes can be brought to be expressed together in an organism. Ligase-assisted reactions have also come to play an increasing role in gene detection. The principle employed in such reactions is that two probe-segments, complementary to target sequences situated in juxtaposition, are joined to a contiguous probe sequence through the agency of a DNA ligase. This is in contrast to more conventional detection schemes where the hybridization of single probes to target sequences is detected after removal of free probe molecules.

One type of ligase-assisted detection method is disclosed in U.S. Pat. No. 4,988,617, which relates to an assay for determining the nucleic acid sequence in a region of a nucleic acid test substance which has a known possible mutation in at least one target nucleotide position of the sequence. The assay comprises annealing two oligonucleotide probes to immediately adjacent segments of a substantially complementary test DNA or RNA molecule which contains the possible mutation(s) near the segment joint, and adding a linking agent, usually a ligase. The conditions are selected such that when the target nucleotide is correctly base paired, the probes are covalently joined, and if not correctly base paired due to a mismatching nucleotide(s) near the the segment joint, the probes are incapable of being covalently joined by the ligase. The presence or absence of linking is detected as an indication of the sequence of the target nucleotide.

A similar ligase-assisted detection method is disclosed in EP-A-185 494. In this method, however, the formation of a ligation product depends on the capability of two adjacent probes to hybridize under high stringency conditions rather than on the requirement of correct base-pairing in the joint region for the ligase to function properly as in the above U.S. Pat. No. 4,988,617. Other references relating to ligase-assisted detection are, e.g., EP-A-330 308, EP-A-324 616, EP-A-473 155, EP-A-336 731, U.S. Pat. No. 4,883,750 and U.S. Pat. No. 5,242,794.

The principal advantages of ligase-based detection strategies over other molecular genetic detection reactions are at least three-fold:

(i) The reaction is inherently very specific. Ligation reactions are based on the coincidence of two separate probe sequences on a target sequence, and this is unlikely to occur in the absence of the appropriate target molecule even under non-stringent reaction conditions. For this reason the reaction is suitable in standardized, automated schemes.

(ii) The ligation reaction can be employed to assess the accuracy of hybridization at positions immediately surrounding the junction between two probes. Due to the substrate requirements of ligases, terminally mismatched probes are ligated at a substantially reduced rate. In this manner, allelic sequence variants can be distinguished.

(iii) The act of ligation creates a unique molecule, not previously present in the assay. This circumstance can be employed, for example, by taking advantage of the increased hybridization stability upon ligation.

JP-A-4262799 and JP-A-4304900 both disclose the use of ligation reactions combined with amplification reactions for detecting a target nucleic acid sequence in a specimen sample. The methodology comprises contacting the sample in the presence of a ligase with a straight chain probe polynucleotide, which has a sequence designed to be cyclized, or circularized, as the result of the presence of a target nucleic acid sequence. The cyclized polynucleotide is then used as a template in an enzymatic polymerization reaction. By adding a primer which is at least partially complementary to the cyclized probe together with a nucleic acid polymerase and nucleotide triphosphates, a single stranded chain nucleic acid is formed which has a repeated sequence complementary to the probe and at least partially to the template. The amplification product is then detected either via a labelled nucleic acid triphosphate incorporated in the amplification, or by an added labelled nucleic acid probe capable of hybridizing to the amplification product.

While this prior art technique comprises a ligase-based detection step, which as discussed above, per se may provide for high specificity, the specificity of the method will rather depend on the specificity in the generation and detection of the amplified product.

SUMMARY OF THE INVENTION

By contrast, the present invention provides a method based upon probe circularization but in which the potential specificity and binding stability of a circularizable DNA probe is fully utilized.

Thus, in accordance with the present inventive concept, efficient use is made of the fact that a probe, designed to be circularized in the presence of a target sequence, may be caused to close around the target-containing nucleic acid strand or strands, for example DNA or RNA, such that the cyclic probe will interlock with and thereby be efficiently linked to the target nucleic acid to be detected. In other words, because of the helical nature of double-stranded nucleic acids, such as DNA, circularized probes will be wound around the target strand, topologically connecting probes to target molecules through catenation, in a manner similar to "padlocks". Such covalent catenation of probe molecules to target sequences results in the formation of a hybrid that resists extreme washing conditions, serving to reduce non-specific signals in genetic assays, as will be further described below. Any probes hybridizing in a non-specific manner may therefore be efficiently removed by subjecting the target to non-hybridizing conditions and/or exonuclease activity. Provided that the circular probe is properly detectable, such as suitably labelled, it may then be detected to indicate the presence of the target molecule. Although the target is not amplified, highly sensitive detection is possible through efficient reduction of non-specific signals.

In a variant of the above strategy, the probe is designed to hybridize to the target sequence with an interspace between the probe ends, and at least one other, or intermediate, probe is provided which is designed to hybridize with the interspatial target sequence. The probes are then interconnected to form a cyclized molecule.

In another variant, the probe is designed to hybridize to the target sequence with a small gap of from one to a few nucleotides between the probe ends. This gap is then filled by an enzyme-assisted extension reaction, such as by DNA polymerase, prior to connecting the probe ends with each other as is per se known in the art. It is readily appreciated that increased specificity may be obtained if such a gap does not contain all four nucleotides.

Both of the above variants will provide for increased specificity of the detection.

This proposed method of the invention, while having a higher specificity, is simpler to perform than the prior art method discussed above. Further, the novel method may be performed with even very short synthetic probes since only part of the probe molecule needs to form a rigid double-stranded DNA molecule with the target molecule, whereas the rest of the probe molecule may be highly flexible, optionally branched single-stranded DNA or any other spacer material. By contrast, a probe that will be replicated, as in the prior art technique, would be expected to require a length in excess of 100 nucleotides and with no non-nucleotide segment and no branched positions.

One aspect of the present invention therefore relates to an assay method of detecting a target nucleic acid sequence in a sample by contacting the sample with a detectable probe to hybridize the probe to the target sequence, and detecting the hybridized probe, which method comprises the steps of:

a) providing a detectable probe, which optionally may be branched and which has two nucleic acid end parts at least partially complementary to and capable of hybridizing to two at least substantially neighbouring regions of the target sequence, b) hybridizing the probe to the target sequence under hybridizing conditions, c) covalently connecting the ends of the hybridized probe with each other to form a circularized-structure, which interlocks with the target strand through catenation, d) subjecting the target sequence to non-hybridizing conditions and/or exonuclease activity to remove any non-circularized probe from the target sequence, thereby retaining only the circularized probe bound to the target molecule, e) optionally repeating steps b) to d) one or more times, and f) detecting the presence and, if desired, location of remaining probe as indicative of the presence of the target nucleic acid sequence.

Another aspect of the invention relates to a nucleic acid detecting reagent, or probe, comprising a structure having an intermediate part, labelled with at least one detectable tag, and two nucleic acid end parts at least partially complementary to and capable of hybridizing to two at least substantially neighbouring respective regions of a target nucleic acid sequence to form a cyclized structure.

The probe does preferably not contain more than about 200 bases (i.e. nucleotides), and may, for example, contain from about 10 to about 100 bases, preferably from about 20 to about 100 bases.

While the probe may be completely composed of DNA or RNA or analogous matter, it is, however, sufficient that only the hybridizing ends thereof consist of nucleic acid or analogous matter. The rest of the probe molecule, i.e. the intermediate part, may very well have any other desired composition.

The probe molecule may be free or immobilized to a solid phase. In the latter case, the method of the invention may also be used for selectively isolating a target nucleic acid sequence from a solution. This may be used for preparative purposes, such as for screening DNA or RNA libraries.

Still another aspect of the invention relates to a kit for detecting a target nucleic acid sequence in a sample, which kit comprises a nucleic acid reagent as described above and ligating means for connecting the reagent ends to each other after hybridization to the target sequence.

BRIEF DESCRIPTION OF THE DRAWINGS

Hereinafter, the invention will be described in more detail with reference to the accompanying drawings, where.

DETAILED DESCRIPTION

Figure 1:
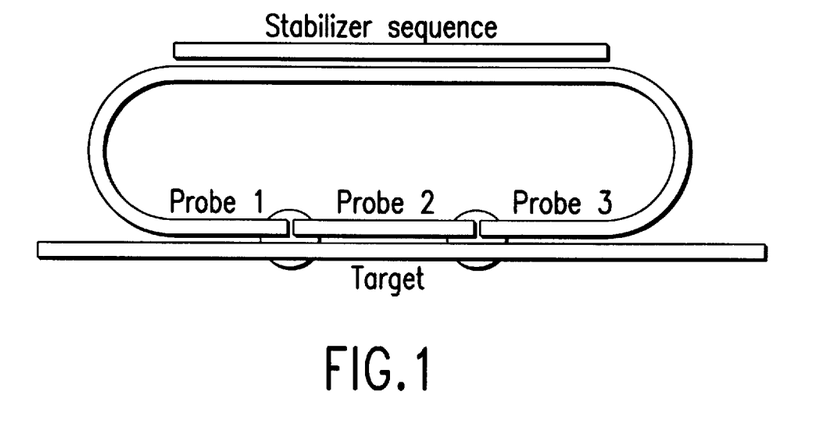
FIG. 1 is a schematic illustration of a probe system hybridized to a target nucleic acid sequence and circularized in accordance with the invention.

Illustrated in FIG. 1 is a detecting reagent according to the invention hybridized to a target nucleic acid sequence, such as a DNA strand, via two end segments of the detecting reagent, designated Probe 1 and Probe 3, the latter being complementary to two respective non-contiguous sequences of the target molecule. An additional probe, designated Probe 2, is hybridized to the intermediate segment of the target molecule with the probe ends in juxtaposition to Probe 1 and Probe 3, respectively. In the illustrated case, the detecting reagent is stabilized by an optional stabilizer sequence to prevent the ends of Probe 1 and Probe 3 from directly contacting each other. The segment of the detecting reagent between the probes may include at least one detectable element, such as a fluorophore.

After Probes 1, 2 and 3 have hybridized to the target molecule, or simultaneously therewith, the probe ends are connected to each other, such as ligated by a ligase, to form a covalently closed circular molecule. Exemplary ligases are T4 DNA ligase, T7 DNA ligase, *E. coli* DNA ligase, and *Thermus thermophilus* DNA ligase. Alternative ways of such covalent closure are, for example, ribozome and chemical ligation. By selecting the length of the detecting reagent as well as the combined length of the probe segments properly, the formed molecule circle will be wound around and interlock with the target molecule. The circularized molecule will then remain linked to the target molecule also under conditions that would release or degrade any hybridized non-cyclized probe and thereby be selectively detectable, indicating the presence of the target molecule in a sample. Thereby the influence of possible hybridization to irrelevant sequences will be completely eliminated.

Conditions that will denature or degrade a hybridized but non-cyclized probe include heat, alkali, other denaturants or exonuclease activity, the latter attacking free ends of uncyclized probes.

While intermediate Probe 2 may be advantageous from the viewpoint of specificity, such an intermediate probe is not critical and the method of the invention may readily be performed without it, i.e. that Probes 1 and 3 are designed to hybridize end to end on the target molecule, whereupon these two ends are ligated to circularize the detecting reagent.

Figure 2:
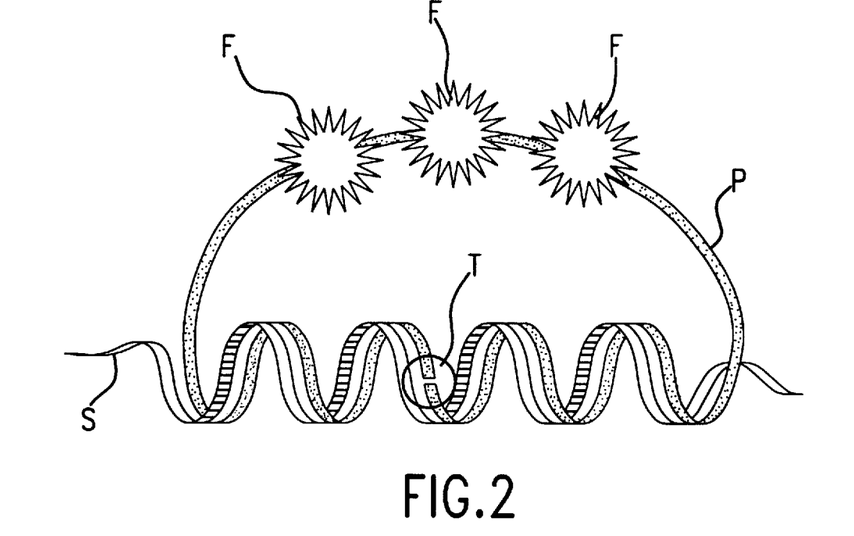
FIG. 2 is a schematic representation of a circularized probe catenated to a target sequence.

The latter, single probe case is illustrated in FIG. 2 which shows a linear probe P, the ends of which are complementary to adjacent regions of a target sequence strand S such that they hybridize to the target sequence juxtaposed to each other. The abutting probe ends are connected to each other at the junction T, such as by a ligase, to circularize the probe P. As may be seen from the figure, due to the helical nature of double-stranded nucleic acid, such as DNA, the hybridizing part of the probe is wound around the target strand and is thereby securely linked to the target strand and cannot be removed even at conditions which interrupt base pairing between complementary DNA strands. The designations F indicate labels, such as fluorophores, on the probe P which permit the catenated probe to be detected by suitable detecting means known in the art, e.g. a photodiode or a CCD detector.

The detection signal may be increased by repeating the cyclizing and dehybridizing steps one or more times. Hereby, on one hand, it will be ensured that allele-specific probes will find and ligate on target molecules, and, on the other hand, it is possible that under certain conditions more and more probes may successively be threaded on the target molecule, as the cyclized probe will move, or wander, to some extent along the molecule during the dehybridizing step, making the target sequence available to a renewed hybridization by a non-circularized probe. For such a multiple introduction of cyclized probe, it is, of course, necessary that the target sequence is at a sufficient distance from the ends of the target molecule, usually at least about 200 base pairs from the nearest end depending on whether and how the target sequence is bound to the support. If the target sequence is free in solution, a longer distance may be required, especially in the case of long-lasting denaturing washes.

The advantages of detecting a covalently closed circular molecule after subjecting the target to non-hybridizing conditions rather than detecting a conventional labelled straight chain probe under hybridizing conditions are several-fold. Firstly, the ligation reaction provides prominent specificity of detection, using single, synthetic probe molecules in total genomic DNA as terminally mismatched probes are poor substrates for ligases. Secondly, the probes circle around or catenate with the target sequences and become covalently linked to the target sequence, thereby becoming substantially insensitive to denaturants. Further, the ends of the detecting reagent become unavailable to exonuclease digestion, aiding in or replacing washes. Thirdly, the simultaneous presence of two terminal probe sequences on one molecule confers kinetic advantages in the hybridization step. Finally, allelic sequence variants can be distinguished by the ligase.

The detecting reagent may, for example, be a 5'-phosphorylated oligonucleotide. As already mentioned above, it is, however, sufficient for the purposes of the present invention that only the actual probe segments consist of nucleotides or optionally functionally analogous structures, such as PNA (peptide nucleic acid), whereas, as already mentioned above, the intermediate segment may wholly or partially have another chemical composition, such as, for example, include residues selected from peptides or proteins, carbohydrates or other natural or synthetic polymers. Such an intermediate structure of non-nucleotide nature may even be preferred with regard to stability and ease of introducing-labels or tags, and also since a non-nucleotide intermediate structure will not exhibit a secondary structure or cause mishybridization.

When used, the stabilizer sequence should preferably have the same length as the sum of the probes, such as 40 or 50 nucleotides. The illustrated curved segments in FIG. 1 would then require, say, of the order of 3 nucleotides.

The combined lengths of the probe sequences should preferably be such that the strands will leave the double helix on the same face 10 or a multiple of 10 bases apart, 10 bases representing approximately one turn of the DNA double helix.

The detecting reagent may be a free molecule or may be immobilized to a support.

The target nucleic acid molecule, which may be DNA or RNA and which contains the specific sequence to be detected, should have a sufficient length to ensure that it can form a double helix, which is required for the circularized probe to interlock or catenate with the target molecule. The target molecule may be a free molecule, but when the detecting reagent is a free molecule, the target molecule is preferably immobilized to a support. When both the probe and the target molecule are free molecules, probe circularization and catenation with the target molecule may, for example, be detected by electrophoretic separation or by other techniques known per se in the art for detecting the formation of the stable complex. In the hybridization, the target molecule is preferably provided in single-stranded form.

Figure 3:
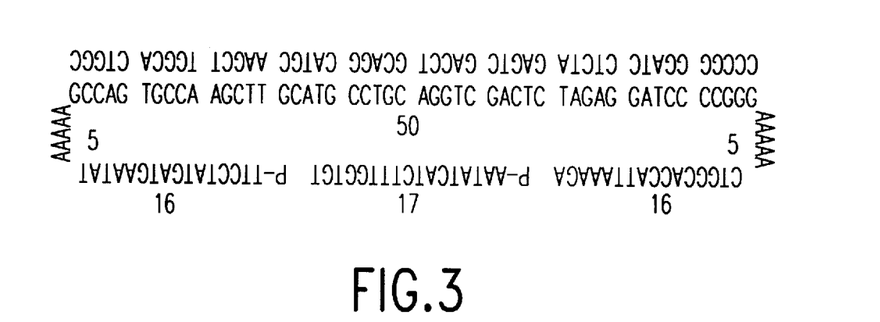
FIG. 3 is an exemplary representation of a detection cassette comprising two probes (SEQ ID NO:3, NO:4, and NO:5)
Figure 4:
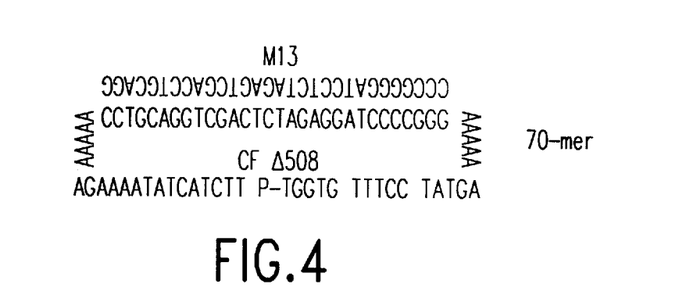
FIG. 4 is an exemplary representation of a detection cassette comprising a single probe (SEQ ID NO:6 and NO:7)

FIGS. 3 and 4 show two specific examples of "detection cassettes" comprising a detecting reagent of the invention. In FIG. 3 the detecting reagent is a stabilized 92-mer (SEQ ID NO:4) to be cyclized together with an intermediate 17-mer (SEQ ID NO:5) (as in FIG. 1), whereas in FIG. 4 the detecting reagent is a 70-mer (SEQ ID NO:7) to be cyclized end to end with itself.

The labels or tags may, for example, be those conventionally used in the art, such as fluorophores, dyes, enzymes, luminescers, radiolabels or affinity groups. When the probes contain branched positions, the detectable groups may advantageously be bound to branches protruding from the cyclized probes. In the case of nucleic acid branches, such branches will permit template-dependent, highly specific and covalent addition of the detectable groups to the cyclized molecules.

Use of the detecting reagent and method of the invention permits the detection of target sequences in situ in tissue sections or in cytological preparations as well as in metaphase or interphase chromosomes. Due to the high specificity, large numbers of target sequences may be analyzed in parallel, preserving spatial information and with a potential to distinguish among allelic sequence variants. The method of the invention will therefore be useful for diagnostic screening at the level of chromosomes or chromatin fibres. Increased signal may be obtained by secondary ligation of detectable molecules to the linker segment of bound probes.

As mentioned above, the inventive concept may also be used for preparative purposes to screen a nucleic acid library in order to isolate clones harbouring a particular target sequence. To this end, the detecting reagent, or probe, is immobilized to a solid phase, such as a membrane. The probe may, for example, consist of two target-complementary regions separated by a non-nucleotide segment containing primary amine groups, e.g. of ethyleneglycol residues interrupted by nucleotide carbon (C) residues, modified with primary amines. These amine groups on the probes are reacted with the membrane and covalently coupled at high density.

The nucleic acid library to be screened for the target complementary region may, for example, be DNA cloned in an M13 vector, or in a plasmid or phagemid vector that permits the excision of inserts as circular plasmids.

To screen such a library of single stranded or double stranded circular molecules, the library is incubated with the probe-containing membrane or membranes, and, after washes, the specifically hybridized probe ends are ligated. After highly stringent washes, removing non-specifically bound molecules, one arm of the probe is cut, e.g. enzymatically, and the target sequence-containing molecules are released in a subsequent denaturation step. If the target sequence-containing molecules are single stranded, these are repaired in solution using, e.g., a primer, T7 polymerase and T4 DNA ligase, and then used to transform bacteria. These bacteria will then propagate the specific target sequence.

The fact that the circularizable reagents, or probes, used in the present invention provide sufficient specificity to detect the location of a unique sequence in total human DNA, and that they recognize very small target sequences, makes it possible to study the nature of unamplified genomic DNA molecules and may permit detection of properties, such as methylation, that may be involved in the development of malignancies.

The invention will now be illustrated further, by way of example only, by the following non-limiting specific Examples.

EXAMPLE 1

Detection of M13mp18 polylinker

An oligonucleotide having the following sequence: 5' P-TGG TGT TTC CTA TGA (TTC*TT)$_{10}$ AAG AAA TAT CAT CTT-OH 3', (SEQ ID NO:1) wherein C* is a cytosine residue biotinylated via a hexamethylenediamine linkage, was synthesized using a commercial DNA synthesizer. The two ends of the oligonucleotide were capable of base-pairing adjacent to each other with the polylinker of the single-stranded, circular bacteriophage M13mp18.

0.1 pmol of the above oligonucleotide was allowed to hybridize to the polylinker of M13mp18 added at 0.36 pmol in a solution containing 5 mM ATP, 1 $\mu$l of One-Phor-All Buffer (10 mM tris-Ac, pH 7.5, 10 mM Mg(Ac)$_2$, 50 mM KAc; Pharmacia LKB Biotechnology AB, Uppsala, Sweden), 1 $\mu$l of T4 DNA ligase (5 U/$\mu$l, Pharmacia LKB Biotechnology AB) in 10 $\mu$l. After incubation over-night, washing was performed under non-hybrizing conditions, and the presence of the radioactive label was detected, indicating that the oligonucleotide had been strongly linked to the single-stranded M13 molecule.

EXAMPLE 2

Detection of CF-mutation delta508

A. DNA fragments including the CF-mutation delta508 or the normal variant of this sequence were cloned in the pUC19 vector in a conventional manner. The two recombinant plasmids obtained were bound to four membrane strips, designated E, F, G and H, by a conventional dot-blot method, 35 ng plasmid (normal or mutant) per dot and two dots per membrane strip, i.e. one with normal DNA and one with mutant DNA. The membranes were washed by pouring boiling water over them and adding SDS to a final concentration of 0.1%. They were then left for 10 minutes, whereupon the membranes were rinsed at room temperature in phosphate-buffered saline (PBS) for 10 minutes to remove plasmids that had not been fixed to the membrane.

A 30 nt biotin-labelled bligonucleotide probe containing a spacer segment and with the following sequence was prepared in a per se conventional manner: 5' P-TGG TGT TTC CTA TGA - X - AAG AAA TAT CAT CTT 3'(SEQ ID NO:2) wherein X is a linking structure -(PEG)$_2$-CB-(PEG)$_2$-CB-(PEG)$_2$-CB-(PEG)$_2$-CB-(PEG)$_2$-, where PEG represents polyethylene glycol residues and CB represents carbon (C) residues having amino functions (NH$_2$) to which biotin residues had been coupled by means of a biotin-NHS ester (Clonetech Laboratories) as described by C. Sund et al., Nucleos. Nucleot. 7, 655 (1988).

The polyethylene glycol (PEG) residues were introduced during the oligonucleotide synthesis using a PEG phosphoramidite as described by A. Jäschke et al., Tetrahedron Lett. 34(2), 301–4 (1993). The molecule was radioactively labelled by adding a $^{32}$p group to the 5'-end of the molecule by means of the enzyme T4 polynucleotide kinase.

The DNA ends of the probe were designed to base-pair end to end with the 100 bp target normal sequence. In contrast, the mutant target is lacking three nucleotides, corresponding to the junction of the probe segments and fails to support the enzymatic joining of these. 15 pmoles of the probe were allowed to hybridize with the target sequence for 30 minutes in a water volume of 500 $\mu$l containing 500 $\mu$g/ml of single-stranded plasmid DNA (salmon sperm DNA), 5xSSPE (1xSSPE=180 mM NaCl, 10 mM NaH$_2$PO$_4$, 1 mM EDTA, pH 7.4), and 5xDenhardt's blocking solution (as defined in Maniatis et al., Molecular Cloning; A Laboratory Manual, Cold Spring Harbour Press 1982).

Ligation was performed with membrane strips E and G in 500 $\mu$l of 0.2M NaCl, 1 mM ATP, 1xOne-Phor-All Buffer (Pharmacia LKB Biotechnology AB), and 0.15 U/$\mu$l T4 DNA ligase (Pharmacia LKB Biotechnology AB).

The membrane strips G and H were then washed in 1 ml of 1xSSPE, 2% SDS for 30 minutes, whereas membrane strips E and F were treated with 500 $\mu$l of 0.2M NaOH for 5 minutes to denature the DNA. The membranes were subsequently washed in 1 ml of 1xSSPE, 2% SDS for 30 minutes, and then soaked in a solution (5xSSPE, 5xDenhardt's blocking solution) also containing 0.1 $\mu$g/500 $\mu$l of streptavidin-horseradish peroxidase (HRP) conjugate (Sigma) for 5 minutes. After rinsing in PBS for 30 minutes, the membranes were put in a solution of ECL solution A mixed with solution B (Amersham, U.K.) for 1 minute and then left to dry for a few seconds on a 3MM paper. The membranes were then placed in a plastic film and put on an X-omat-S film and exposed for 1 second—1 minute. The results are shown in FIG. 5, where dots with the correct target sequence are to the right (designated N) and the dots with the mutant sequence are to the left (designated M) in the figure.

Figure 5:
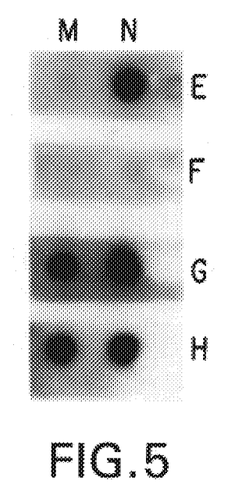
FIG. 5 is a photograph of four blotting membranes showing the results of hybridization of a probe to a target molecule in accordance with the method of the invention as well as under other conditions.

From FIG. 5 it is seen that on the membrane strips treated under non-denaturing washing conditions (strips G and H), both allele variants of the target sequence were detected whether ligase treated or not.

If, however, the membranes were washed with an alkali denaturant, only the correct signal, i.e. detection of normal DNA, was obtained (ligase-treated membrane E), whereas if no ligase was added, neither target sequence was detected after alkali treatment (membrane F).

Thus, hybridization with the addition of ligase and wash with denaturant ensures that only the desired, i.e. normal DNA sequence is detected.

B. Eight membrane strips, numbered 1–8, were prepared with two dots of 35 ng plasmid (normal or mutant) and subjected to various hybridizing/washing conditions essentially as described above. Membranes 1–5 were hybridized with 1, 5, 10 and 15 pmoles, respectively, of the probe, then treated with ligase—except membrane 5—and washed with 0.2M NaOH for 5 minutes. Membranes 6–8 were all hybridized with 15 pmoles of the probe, treated with ligase and then washed, each with a different agent, viz. boiling 0.5× SSPE (6), boiling 0.1% SDS (7) or 0.2M NaOH (8) (10 min.). The results are shown in FIG. 5, where the dots with the correct target sequence (N) are those to the right in the figure, whereas those with the mutant target sequence (M) are those to the left.

Figure 6:
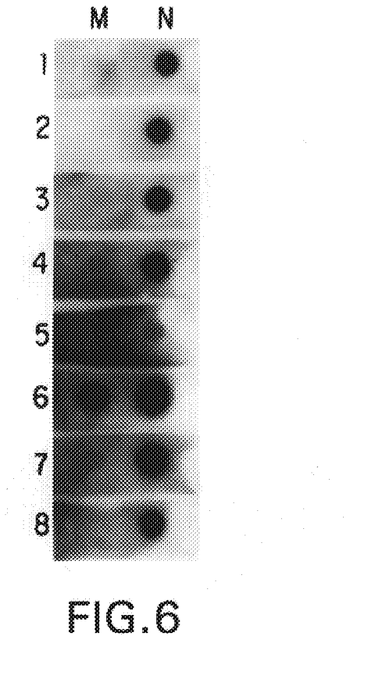
FIG. 6 is a similar photograph as that of FIG. 5 showing eight blotting membranes carrying target molecules hybridized with a probe and treated under various conditions.

As is demonstrated by FIG. 6, the detection is ligase-dependent if the membranes are washed with alkali or boiling SDS, whereas a non-stringent wash (membrane 6) did not remove the probe hybridized to the incorrect target sequence.

Figure 7:
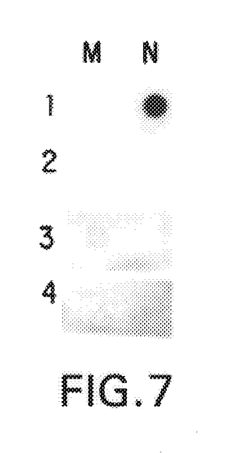
FIG. 7 is a photograph of four blotting membranes hybridized with either a circularizable probe or two linear probes corresponding to the respective hybridizing end segments of the circularizable probe.

C. Four membrane strips were prepared with normal and mutant plasmid dots, respectively, and hybridized with either the biotin-labelled probe prepared in section A above (strips 1 and 2) and two linear probes corresponding to the two oligonucleotide segments of the probe (strips 3 and 4). Membrane strips 1 and 3 were then treated with ligase, whereupon all membranes were washed with 0.2M NaOH. The results are shown in FIG. 6, "N" and "M" designating normal and mutant plasmid, respectively. As appears from FIG. 7, only the ligase-treated circularized probe remained on the membrane after washing.

EXAMPLE 3

Effect of distance from target sequence to the end of the target molecule

Figure 8:
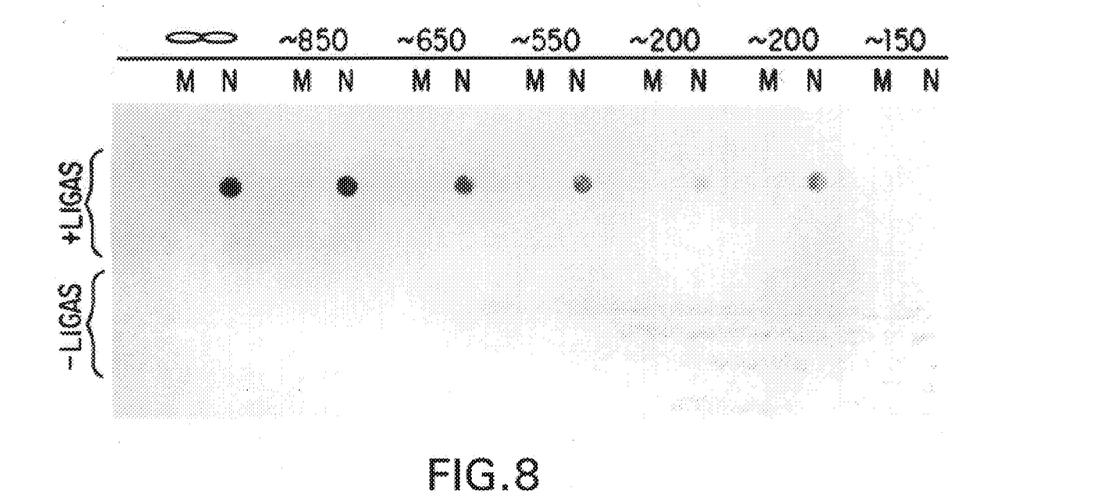
FIG. 8 is a photograph of blotting membranes where the probe used in FIG. 6 has been circularized to restriction fragments of the target molecule in FIG. 6.

The target molecule in Example 2 was cleaved by restriction enzymes into fragments having the target sequence located at a distance of about 850, 650, 550 and 200 base pairs, respectively, from the molecule end. In the same way as described in Example 2A, the plasmids were immobilized on nylon membranes, probed by hybridization with the circularizable oligonucleotide in Example 2, either subjected to a ligation step or not, and subsequently subjected to a denaturing wash in 0.2M NaOH. The results are shown in FIG. 8, where "∞" represents the uncleaved molecule, and "N" and "M" designate normal and mutant plasmid, respectively. The results demonstrate that when the distance to the end of the target molecule is less than about 200 base pairs, the circularized probe will tend to slide off the target molecule during the wash step.

The invention is, of course, not restricted to the embodiments specifically described above and shown in the drawings, but many modifications and changes can be made within the scope of the present inventive concept as defined in the following claims.

What is claimed is:

1. A method of detecting a target nucleic acid sequence in a sample, said method comprising
   a) providing a detectable probe having two free nucleic acid ends which are at least partially complementary to and capable of hybridizing to two adjacent regions of said target sequence;
   b) hybridizing said probe ends to said target sequence under hybridizing conditions;
   c) covalently connecting said ends of said hybridized probe with each other to form a circularized structure which interlocks with said target sequence through catenation;
   d) subjecting said target sequence and said probe to non-hybridizing conditions and optionally to exonuclease activity, wherein any non-circularized probe is removed from said target sequence;
   e) optionally repeating steps b) to d) one or more times; and
   f) detecting the presence of said probe, wherein the presence of said probe is indicative of the presence of said target nucleic acid sequence.

2. The method according to claim 1, wherein in said step b), said probe ends hybridize to said target sequence to leave an interspace between said probe ends, wherein said step b) further comprises
   b1) providing at least one additional probe having two free nucleic acid ends, wherein said additional probe hybridizes to said target sequence in said interspace, and wherein said step c) comprises
   c) covalently connecting each of said respective ends of said probe in said step a) to the respective adjacent end of said additional probe to form a circularized structure which interlocks with said target sequence through catenation.

3. The method according to claim 1, wherein said probe hybridizes to said target sequence to leave a gap of one or more nucleotides between adjacent probe ends, and wherein said step b) further comprises
   b1) filling said gap by an extension reaction prior to covalently connecting said probe ends.

4. The method according to claim 1 or 3, wherein said covalent connecting of said probe ends is performed by a reaction selected from the group consisting of an enzymatic reaction, a ribozyme-mediated reaction, and a chemical ligation reaction.

5. The method according to claim 1 or 3, wherein said target sequence is a DNA or RNA sequence.

6. The method according to claim 1 or 3, wherein said probe is an oligonucleotide.

7. The method according to claim 1 or 3, wherein said probe further comprises one or more intermediate segments having a nucleic acid composition and wherein said probe is stabilized by hybridization of a stabilizer oligonucleotide sequence to said one or more intermediate segments of said probe.

8. The method according to claim 1 or 3, wherein said probe further comprises one or more intermediate segments having a composition other than nucleic acid.

9. The method according to claim 8, wherein said one or more intermediate segments are comprised of material selected from the group consisting of protein, polypeptide, carbohydrate and a synthetic polymer.

10. The method according to claim 1 or 3, wherein said probe contains from about 10 to about 200 bases.

11. The method according to claim 1 or 3, wherein said target sequence is in single-stranded form.

12. The method according to claim 1 or 3, wherein said probe is immobilized to a solid phase.

13. The method according to claim 1 or 3, wherein said target sequence is immobilized to a solid phase.

14. The method according to claim 13, wherein said sample is a DNA library, wherein said target sequence is DNA, and said method further comprising
   g) cleaving said immobilized circularized probe;
   h) subjecting the probe/target DNA complex to denaturing conditions to release said target DNA sequence; and
   i) transforming bacteria with said target DNA sequence.

15. A method of selectively capturing a target nucleic acid sequence to a solid support, said method comprising
   a) providing a probe having two free nucleic acid ends which are at least partially complementary to and capable of hybridizing to two adjacent regions of said target sequence, and said probe being immobilized to a solid support;
   b) hybridizing said probe ends to said target sequence under hybridizing conditions;
   c) covalently connecting said ends of said hybridized probe with each other to form a circularized structure which interlocks with said target sequence through catentation; and
   d) subjecting said support and said captured target sequence to non-hybridizing conditions, wherein any non-catenated target sequence is removed from said support.

16. The method according to claim 4, wherein said reaction is an enzymatic ligation reaction.

17. The method according to claim 15, said method further comprising
   e) cleaving said probe in a part thereof not participating in the hybridization, wherein said target sequence is released.

18. The method according to claim 2, wherein said probe and said additional probe hybridize to said target sequence to leave gaps of one or more nucleotides between said adjacent ends of said probe and said additional probe, and wherein said step b1) further comprises
   ii) filling said gaps by an extension reaction prior to covalently interconnecting said probe and additional probe ends.

19. The method according to claim 2 or 18, wherein said covalent connection of said probe and said additional probe ends is performed by a reaction selected from the group consisting of an enzymatic reaction, a ribozy-mediated reaction, and a chemical ligation reaction.

20. The method according to claim 19, wherein said reaction is an enzymatic ligation reaction.

21. The method according to claim 2 or 18, wherein said target sequence is a DNA or RNA sequence.

22. The method according to claim 2 or 18, wherein said probe is an oligonucleotide.

23. The method according to claim 2 or 18, wherein said probe further comprises one or more intermediate segments having a nucleic acid composition, and wherein said probe is stabilized by hybridization of a stabilizer oligonucleotide to said one or more intermediate segments.

24. The method according to claim 2 or 18, wherein said probe further comprises one or more intermediate segments having a composition other than nucleic acid.

25. The method according to claim 24, wherein said one or more intermediate segments are comprised of a material selected from the group consisting of protein, polypeptide, carbohydrate, and synthetic polymer.

26. The method according to claim 2 or 18, wherein said probe and said additional probe contain from about 10 to about 200 bases.

27. The method according to claim 2 or 18, wherein said target sequence is in single-stranded form.

28. The method according to claim 2 or 18, wherein said probe is immobilized to a solid phase.

29. The method according to claim 2 or 18, wherein said target sequence is immobilized to a solid phase.

30. The method according to claim 29, wherein said sample is a DNA library, wherein said target sequence is DNA, and said method further comprising g) cleaving said immobilized circularized probe;
   h) subjecting the probe/target DNA complex to denaturing conditions to release said target DNA sequence; and
   i) transforming bacteria with said target DNA sequence.

31. The method according to claim 4, wherein said reaction is a ribozyme-mediated reaction.

32. The method according to claim 4, wherein said reaction is a chemical ligation reaction.

33. The method according to claim 5, wherein said target sequence is a DNA sequence.

34. The method according to claim 5, wherein said target sequence is an RNA sequence.

35. The method according to claim 9, wherein said material is protein.

36. The method according to claim 9, wherein said material is polypeptide.

37. The method according to claim 9, wherein said material is carbohydrate.

38. The method according to claim 9, wherein said material is a synthetic polymer.

39. The method according to claim 19, wherein said reaction is a ribozyme-mediated reaction.

40. The method according to claim 19, wherein said reaction is a chemical ligation reaction.

41. The method according to claim 21, wherein said target sequence is a DNA sequence.

42. The method according to claim 21, wherein said target sequence is an RNA sequence.

43. The method according to claim 25, wherein said material is protein.

44. The method according to claim 25, wherein said material is polypeptide.

45. The method according to claim 25, wherein said material is carbohydrate.

46. The method according to claim 25, wherein said material is a synthetic polymer.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
TGGTGTTTCC  TATGATTCTT  TTCTTTTCTT  TTCTTTTCTT  TTCTTTTCTT  TTCTTTTCTT        60

TTCTTAAGAA  ATATCATCTT                                                        80
```

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear     ( i i ) MOLECULE TYPE: cDNA     ( i x ) FEATURE:
        ( A ) NAME/KEY: misc_feature (B) LOCATION: 16
(D) OTHER INFORMATION: /note= "N= LINKING STRUCTURE"

(x i) SEQUENCE DESCRIPTION: SEQ ID NO:2:

TGGTGTTTCC TATGANAAGA AATATCATCT T                                31

(2) INFORMATION FOR SEQ ID NO:3:

(i) SEQUENCE CHARACTERISTICS:
(A) LENGTH: 50 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:3:

CCCGGGGATC CTCTAGAGTC GACCTGCAGG CATGCAAGCT TGGCACTGGC             50

(2) INFORMATION FOR SEQ ID NO:4:

(i) SEQUENCE CHARACTERISTICS:
(A) LENGTH: 92 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:4:

TTCCTATGAT GAATATAAAA AGCCAGTGCC AAGCTTGCAT GCCTGCAGGT CGACTCTAGA   60

GGATCCCCGG GAAAAACTGG CACCATTAAA GA                                92

(2) INFORMATION FOR SEQ ID NO:5:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:5:

AATATCATCT TTGGTGT                                                 17

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:6:

CCCGGGGATC CTCTAGAGTC GACCTGCAGG                                   30

(2) INFORMATION FOR SEQ ID NO:7:

(i) SEQUENCE CHARACTERISTICS:
(A) LENGTH: 70 base pairs
(B) TYPE: nucleic acid
(C) STRANDEDNESS: single
(D) TOPOLOGY: linear (i i) MOLECULE TYPE: cDNA ( x i ) SEQUENCE DESCRIPTION: SEQ ID NO:7:

```
TGGTGTTTCC  TATGAAAAAA  GGGCCCCTAG  GAGATCTCAG  CTGGACGTCC  AAAAAAGAAA    60
ATATCATCTT                                                                70
```